United States Patent [19]
Thompson et al.

[11] Patent Number: 5,269,189
[45] Date of Patent: Dec. 14, 1993

[54] METHOD AND MEANS OF TRANSMITTING AND RECEIVING BROAD-BAND UNIPOLAR, ULTRASONIC PULSES FOR ULTRASONIC INSPECTION

[75] Inventors: Donald O. Thompson; David K. Hsu, both of Ames, Iowa

[73] Assignee: Iowa State University Research Foundation, Inc., Ames, Iowa

[21] Appl. No.: 477,162

[22] Filed: Feb. 8, 1990

Related U.S. Application Data

[63] Continuation of Ser. No. 181,094, Apr. 13, 1988, abandoned.

[51] Int. Cl.$^5$ ............................................. G01N 29/00
[52] U.S. Cl. ..................................... 73/632; 73/642
[58] Field of Search ................ 73/609, 610, 620, 629, 73/632, 642; 367/135, 137

[56] References Cited

U.S. PATENT DOCUMENTS

| | | | |
|---|---|---|---|
| 3,334,622 | 8/1967 | Brech | 128/2 |
| 3,387,257 | 6/1968 | Brech | 340/15 |
| 3,733,891 | 5/1973 | Weighart | 73/67.9 |
| 3,823,603 | 7/1974 | Couture | 73/67.9 |
| 3,876,938 | 4/1975 | Ohta | 325/22 |
| 4,041,774 | 8/1977 | Morris et al. | 73/67.9 |
| 4,114,457 | 9/1978 | Thun | 73/632 |
| 4,168,629 | 9/1979 | Bulteel | 73/615 |
| 4,221,132 | 9/1980 | Poole | 73/620 |
| 4,277,978 | 7/1981 | Puckette | 73/632 |
| 4,391,142 | 7/1983 | Cantrell, Jr. et al. | 73/610 |
| 4,432,235 | 2/1984 | Renzel et al. | 73/611 |
| 4,539,617 | 9/1985 | Delaney et al. | 361/58 |
| 4,566,331 | 1/1986 | Schroeder | 73/632 |
| 4,817,016 | 3/1989 | Thompson et al. | 364/507 |

FOREIGN PATENT DOCUMENTS 57-19579  11/1982  Japan .

OTHER PUBLICATIONS

Krautkramer et al., "Ultrasonic Testing of Materials", 2nd Ed., Springer-Verlag, New York, 1977, pp. 148 & 204.

Millman, J., "Microelectronics", (1979), p. 240, 573-575.

Primary Examiner—Louis Arana
Attorney, Agent, or Firm—Zarley, McKee, Thomte, Voorhees & Sease

[57] ABSTRACT

The invention includes a means and method for transmitting and receiving broadband, unipolar, ultrasonic pulses for ultrasonic inspection. The method comprises generating a generally unipolar ultrasonic stress pulse from a low impedance voltage pulse transmitter along a low impedance electrical pathway to an ultrasonic transducer, and receiving the reflected echo of the pulse by the transducer, converting it to a voltage signal, and passing it through a high impedance electrical pathway to an output. The means utilizes electrical components according to the method. The means and method allow a single transducer to be used in a pulse/echo mode, and facilitates alternatingly transmitting and receiving the broadband, unipolar, ultrasonic pulses.

20 Claims, 9 Drawing Sheets

METHOD AND MEANS OF TRANSMITTING AND RECEIVING BROAD-BAND UNIPOLAR, ULTRASONIC PULSES FOR ULTRASONIC INSPECTION

This invention was made with Government support under Contract No. 7405 ENG 82, awarded by the Department of Energy. The Government has certain rights in the invention.

This is a continuation of copending application Ser. No. 07/181,094, filed on Apr. 13, 1988, now abandoned.

BACKGROUND OF THE INVENTION

Non-destruction evaluation (NDE) is becoming an increasingly valuable tool in many aspects of industry, research, and technology development. One promising method of NDE is the use of ultrasound to investigate materials and structures with no adverse effect on the material or structure.

The ways in which ultrasound is sent through and into a material, and then its echos received, are many and well known. Presently, the most significant problems involve the ability to understand the content of the ultrasonic echos received back, and to recognize what type of ultrasonic inspection is needed for optimal results.

Recently, significant advances have been made in the mathematical processes which are used to evaluate the received ultrasound. In particular, inverse elastic wave scattering theories have been improved so that they can be applied to different ultrasonic frequency ranges, and different types of material evaluations. For example, using these theories, flaws in a material can be quantitatively approximated as to size, shape, and orientation.

Although the mathematical theories have been advanced to cover wide frequency ultrasound information, as of yet, there has not been a satisfactory means or method for actually generating sufficiently broadband, ultrasonic pulses for transmitting and receiving in ultrasonic NDE inspection to take full advantage of the advances. The state of the art commercial ultrasonic instrumentation and transducers have bandwidths too narrow to adequately employ the inverse scattering theories for a range of different material properties, and most significantly, for a range of flaw sizes.

Without adequate frequency bandwidth, estimates and approximations for ultrasonic NDE evaluation and inspection will have margins of error which are too great for reliability. Furthermore, it disallows application of the ultrasonic inspection to analyze flaws or material properties of various sizes.

It has been determined that one method to improve transducer bandwidth is to utilize unipolar pulses. In one attempt to utilize unipolar pulses, a first transducer, being connected to a low impedance electronic pulser, transmitted an ultrasonic signal to the material being evaluated. A second transducer connected to a high impedance amplifier received the reflection or echo of these ultrasonic pulses. The system tried to emulate unipolar pulses to broaden bandwidth, by utilizing one transducer to "pitch" the ultrasound, and another transducer to "catch" the ultrasound. The transducers of this system are set to be in a pitch-catch mode.

However, NDE ultrasound evaluation most times requires the use of one transducer only for both transmitting and receiving. This is called utilizing the transducer in the "pulse-echo mode". No adequate means or method for generating the desired broadband, unipolar pulses using a conventional planar transducer has been developed.

It is therefore a primary object of the present invention to produce a means and method for transmitting and receiving broadband, unipolar ultrasonic pulses for non-destructive evaluation and inspection which improves over or solves the problems and deficiencies in the art.

Another object of the present invention is to provide a means and method as above described which improves the frequency bandwidth of ultrasound for NDE inspection.

A further object of the present invention is to provide a means and method as above described which presents a low impedance path between the pulse transmitter and the transducer, and presents a high impedance electrical pathway between the transducer and the output.

Another object of the present invention is to provide a means and method as above described which produces broadband, unipolar ultrasonic pulses utilizing a single transducer as both a transmitter and receiver.

Another object of the present invention is to provide a means and method as above described, which improves the reliability and accuracy of evaluation of estimates of ultrasonic non-destructive evaluation.

A further object of the present invention is to provide a means and method as above described which provides accurate and reliable results for a variety of material flaw sizes and material properties.

A further object of the present invention is to provide a means and method as above described which is accurate, reliable, and easily adaptable to a variety of NDE systems.

Another object of the present invention is to provide a means and method as above described which is economical and versatile.

Another object is to provide a means and method as above described which comprises a coupling network for coupling a transmitter, transducer and receiver together to provide a unipolar ultrasonic pulse with low impedance coupling from transmitter to transducer, and high impedance coupling for transducer to receiver. This coupling can be provided as a separate transmit/receive switch or incorporated into the transmitter and receiver to achieve the same results.

These and other objects, features, and advantages of the present invention will become more apparent with reference to the accompanying specification and claims.

SUMMARY OF THE INVENTION

The present invention results in an improvement in bandwidth of ultrasonic pulses generated for ultrasonic non-destructive evaluation of materials. Broadband, unipolar, ultrasonic stress pulses are produced and then utilized to characterize flaws in materials using various inverse methods to measure and characterize a variety of different material properties.

In order to achieve the broader band ultrasonic stress pulses in a conventional planar ultrasonic transducer, unipolar ultrasonic stress pulses are created from a low impedance voltage pulser means connected to the transducer along a low impedance electrical pathway. Conversely, the single transducer receives the ultrasonic echoes and is connected along a high impedance electrical pathway to an output.

A single transducer operates in a pulse-echo mode, alternating between transmitting the unipolar stress pulses, and receiving the unipolar echoes, and then converting them to voltage signals which are sent to the output, where they can then be transmitted to equipment to store, record, and evaluate them.

BRIEF DESCRIPTION OF THE DRAWINGS

FIG. 7A is similar to FIG. 6A except that the FET FIG. 5 is not bypassed.

DETAILED DESCRIPTION OF THE PREFERRED EMBODIMENT

With reference to the accompanying drawings containing FIGS. 1 through 14A and B, a preferred embodiment of the invention will now be described.

Figure 1:
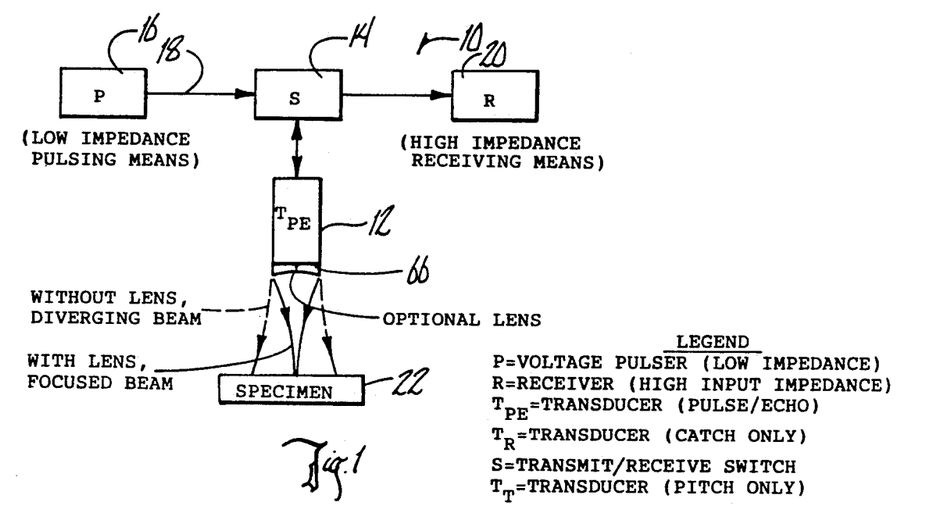
FIG. 1 is a schematic depicting the general configuration of one embodiment of the invention.
Figure 2:
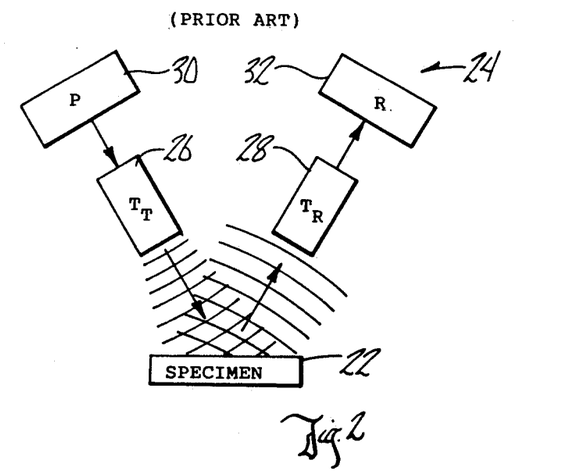
FIG. 2 is a schematic depicting a prior art embodiment.

To aid in an understanding of the invention, reference is taken to FIGS. 1 and 2, which simplistically depict a structural embodiment of the invention as compared to a prior art structure. According to the present invention, FIG. 1 shows an ultrasonic inspection system 10 having a transducer 12 operating in a pulse-echo mode. The pulse-echo mode means that transducer 12 is utilized to both transmit ultrasound stress pulses, and to detect ultrasonic stress pulse echoes, and then convert them into a voltage signal. Transducer 12 is electrically connected to switching circuitry 14 and can both receive and send electrical signals to switching circuitry 14. A low impedance voltage pulse transmitter 16 is connected by low impedance electrical cable 18 to switching circuitry 14. System 10 finally consists of a high input impedance receiving circuitry 20 which receives the voltage signals from transducer 12, which signals represent the received echoes from the ultrasonic stress pulse directed to specimen 22.

It can therefore be seen that system 10 utilizes one transducer 12 in the pulse-echo mode, and operates by generating a voltage pulse from a low impedance pulse transmitter 16 which is sent to transducer 12 to create the stress pulse, and then the switching circuitry 14 operates to send the received echo from transducer 12 to the high impedance receiving circuitry 20. Transmitter 16, in the preferred embodiment, generates a square voltage pulse. System 10 maintains the unipolar nature of the pulse which, as previously described, improves the operating band of the ultrasonic inspection system 10 and produces improved results.

By direct comparison, FIG. 2 shows one prior art arrangement of an ultrasonic inspection system 24 which utilizes a first transducer 26 to transmit the ultrasonic stress pulses, and a second transducer 28 to receive the reflected echo from specimen 22. A pulse transmitter 30 is electrically connected directly to transducer 26, whereas a receiving circuitry 32 is electrically connected directly to transducer 28. In such a configuration, the transducers are set to operate in a "pitch-catch mode"; with the first transducer 26 "pitching" the ultrasonic stress pulse, and transducer 28 "catching" the reflected echo of the pulse. As previously discussed, ultrasonic inspection for non-destructive evaluation of materials cannot be used to its greatest advantage using a pitch-catch configuration, such as is found in the preferred embodiment of system 10 of FIG. 1.

Crucial to the present invention is the implementation of the system whereby there is a low impedance electrical pathway between the transmitter and the pulse-echo transducer when the system is transmitting a stress pulse, and a high impedance electrical pathway between the transmitter and the receiving circuitry during the receiving cycle of the system. It is to be understood that the low and high impedances can also be incorporated directly into the transmitter and receiver, respectively. As previously stated, conventional commercial transducers cannot achieve the sufficient bandwidth for satisfactory results according to the improved mathematics of inverse elastic wave scattering. However, the use of the embodiment of system 10 to create a unipolar transmitted ultrasound stress pulse, and a received ultrasound echo, is one way to improve bandwidth.

Addison, et al., in an article in "Review of Progress in QNDE", Volume I, pages 251-266 (Plenum Press, New York, 1982), showed that the minimum bandwidth needed for sizing flaws with a radius "a", using the simplest, one-dimensional inverse Born scattering solution must extend from ka=0.5 to ka=2.0 in order to achieve sizing accuracies of 20%. Here, "k" is the magnitude of the wave vector and is given by $2\pi/\lambda$ where $\lambda$ is the ultrasonic wave length. Addison, et al., further showed that without this sufficient bandwidth, size estimates would be either too small or too large, depending upon whether there was a deficiency of the low or high frequency content in the interrogating ultrasonic spectrum. If the investigator is analyzing materials with a range of flaw sizes, the problem is magnified.

The advantages of utilizing unipolar pulses to broaden bandwidth have been discussed by a number of authors, for example, Yu, et al., "IEEE Ultrasonic Symposium Proceedings", 1979, pages 284-288; R. B. Thompson, et al., "IEEE Ultrasonic Symposium Proceedings", 1981, pages 930-935; and Muratore, et al., "IEEE Ultrasonic Symposium Proceedings", 1982, pages 1049-1053.

It has further been discovered that a unipolar pulse can be created by applying a step function voltage pulse from a low impedance transmitter to the transducer. See N.E. Dickson and Davis, Battelle Pacific Northwest Laboratories, Report BNWL-1526, CU-37, February, 1971. However, the received echo from the unipolar stress pulse can degenerate into a non-unipolar signal if the impedance of the external circuit or receiving circuit used to measure the signal is low compared to the transducer output impedance.

FIGS. 3A-D and FIGS. 4A-D illustrate such difficulties. It has been discovered that if the quantity $R_L C_o \omega$ is substantially greater than 1, the received signal will not greatly vary from its unipolar nature. However, if this product is substantially less than one, the signal may be differentiated by the measuring or receiving circuit nd lose its unipolar nature. $R_L$ is the impedance of the external circuit used to measure the received signal or echo of the ultrasonic stress pulse, and the product $\omega C_o$ is the reciprocal of the transducer source impedance.

Figure 3A:
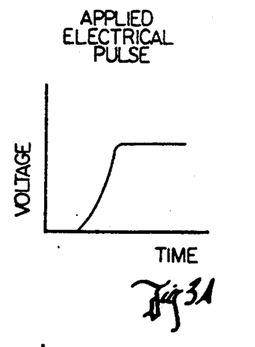
FIGS. 3A-D are graphic representations of transmitted and received pulse shapes from a step function excitation voltage.
Figure 3B:
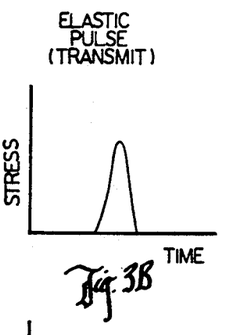
Figure 3C:
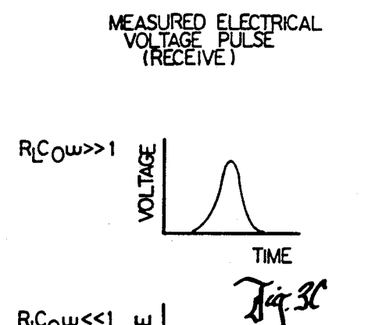
Figure 3D:
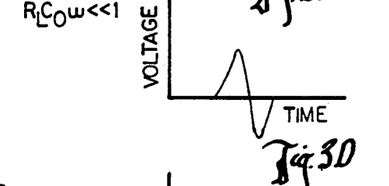

FIGS. 3A-D illustrate this principle. FIG. 3A depicts the shape of a step function voltage pulse. FIG. 3B depicts the general shape of the stress pulse transmitted from the transducer, showing its basically unipolar shape. FIG. 3C shows that if the $R_L C_o \omega$ is substantially greater than one, ($R_L C_o \omega >> 1$), the received measured electrical voltage pulse seen by the receiving circuitry is also generally unipolar in shape. However, FIG. 3D shows that if the product is substantially less than one, ($R_L C_o \omega << 1$), the received voltage degrades into basically a bi-polar pulse.

Figure 4A:
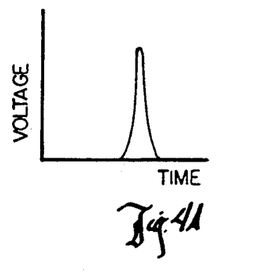
FIGS. 4A-D are graphic representations of transmitted and received pulse shapes for a spike excitation voltage.
Figure 4B:
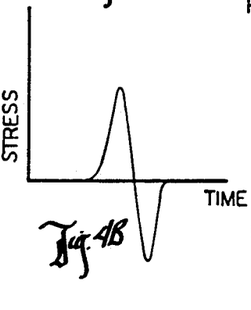
Figures 4C, 4D:
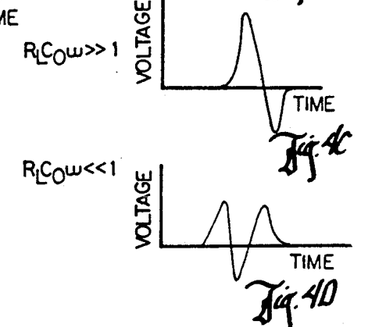

By way of comparison, FIGS. 4A-D show the unsuitability of a conventional spike applied-voltage pulse, (FIG. 4A). The spike voltage pulse applied to the transducer then generates a basically bi-polar stress pulse (FIG. 4B). Depending on whether the product $R_L C_o \omega$ is substantially greater than one or less than one, the received pulse from the bi-polar stress pulse will be respectively bi-polar (FIG. 4C), or tri-polar (FIG. 4D), and not unipolar.

Figure 5:
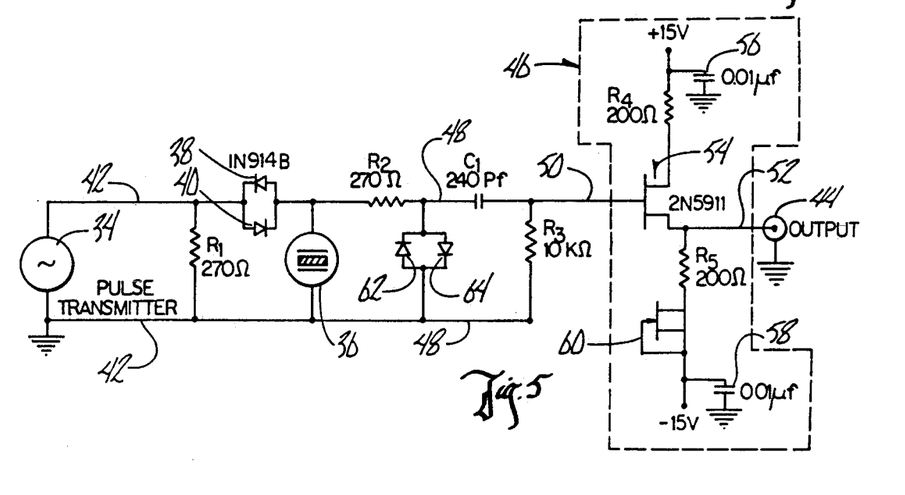
FIG. 5 is a schematic circuit diagram depicting one embodiment of the transmit-receive switch used in producing unipolar ultrasonic pulses.

FIG. 5 therefore depicts the preferred circuitry for generating, transmitting, receiving, and preparing for utilization, a unipolar broadband, ultrasonic pulse for ultrasonic non-destructive evaluation of materials. This circuitry switches between a transmit cycle and a receive cycle while retaining the unipolar broad band characteristics of the pulse. Voltage pulse transmitter 34 produces a step function voltage pulse and can be a Hewlett-Packard 214A or 214B operated from 110 volts AC. Other commercially available pulsers can also be used. A conventional commercially available piezoelectric transducer 36 is electrically connected in parallel with transmitter 34. Transducer 36 can be a Panametrics transducer with a 10 or 25 MHz center frequency and a ¼ inch diameter. It is to be understood that it is important that transducer 36 contain only an internal piezoelectric element and has no internal tuning elements. This is essential because if transducer 36 had tuning elements, it could disrupt the impedance matching required for the successful operation of the invention.

Between transmitter 34 and transducer 36, a pair of diodes 38 and 40 are electrically connected in opposite directions and parallelly along electrical pathway 42. Diodes 38 and 40 are conventional and well known in the art, and can be commercially purchased under the designation IN914D. In the transmit cycle, diodes 38 and 40 present a low impedance pathway between transmitter 30 and transducer 36. However, during the receive cycle, diodes 38 and 40 effectively block any signals between transducer 36 and transmitter 34. This is because the voltage signals produced as a result of the reception of ultrasonic echos by transducer 36 are so small that they cannot cause diodes 38 or 40 to conduct.

Resistor $R_1$ is non-essential to the operation of the circuit according to the invention. Its purpose, however, is to allow multiplexing if the transmitter is switched electronically to alternate transducers, a procedure which is explained by D. 0. Thompson and S. J. Wormley, in "Review of Progress in QNDE", Plenum Press, New York, 1984 4: 287-296. It is connected across parallel sides of the circuitry between transmitter 34 and transducer 36, and its only purpose is to keep the circuit input at ground potential when transmitter 34 is switched to other circuits.

It can therefore be seen that the circuitry between transmitter 34 and transducer 36 provides a low impedance electrical pathway. It is to be understood that diodes 38 and 40, in this preferred embodiment, are essential since the impedance of all current paths from transducer 36 must be included in the calculation of the load impedance $R_L$ presented to transducer 36.

On the opposite side of transducer 36, the circuitry terminates in an electrical output or connection 44, such as is known in the art. Connection 44 is the input of the amplifier in the receiver circuitry. Between transducer 36 and output 44 are the following components. A field effect transistor (FET) buffer 46 is electrically connected in the electrical pathway between transducer 36 and output 44, directly before output 44. FET buffer 46 presents a high impedance input side 50 and a low impedance output side 52, such as is known in the art. In the preferred embodiment of FIG. 5, FET buffer 46 is comprised of FET 54, which can be a FET of product designation 2N5911. FET buffer 46 is operated by plus and minus 15 volts, and has resistors $R_4$ and $R_5$ electrically connected on either side of it, in addition to capacitors 56 and 58, which are 0.01 microfarad capacitors and are electrically connected to ground. The final component of FET buffer 46 is electrical element 60. The configuration of FET buffer 46 is conventional as is known in the art to create a high impedance input side 50 and a low impedance output side 52.

A pair of diodes 62 and 64 are parallelly, but oppositely connected across the parallel sides of the electrical pathway 48. Diodes 62 and 64 can be described as a protective device to shield FET 54 or any following electrical components such as preamplifiers and the like, from what will be called the "main bang" of transmitter 34. Resistor $R_2$ is a parallel load resistor for transducer 36 so that diodes 62 and 64 do not simply short the main transmitter pulse to ground during the transmit cycle. The preferred value of resistor $R_2$ is 270 ohms. It is to be understood that this value is not critical, but must be several times larger than the input impedance of transducer 36 for all operating frequencies.

In the preferred embodiment of the circuitry of FIG. 5, an additional combination of electrical components comprised of resistance capacitance network $R_3C_1$ is electrically connected between transducer 36 and FET buffer 46. Capacitor $C_1$ in the preferred embodiment is 240 picofarads (pf), whereas resistor $R_3$ is 10 Kilo-ohms ($k\Omega$). Network $R_3C_1$ thus produces a time constant of 2.4 microseconds. Network $R_3C_1$ can be selected to produce a desired time constant and to set the low frequency end of the signal band pass. The received signals in the pulse-echo mode from the transducer 36 are coupled to the high impedance FET 54 through network $R_3C_1$. With these values, the low frequency pass limit is 0.4 MHz.

It is to be understood that network $R_3C_1$ also has an impedance. These components ($R_3C_1$) should be chosen with appropriate impedance-affecting values so that the total load impedance presented to transducer 36 is approximately ten to twenty times the source impedance of transducer 36. Although the actual values of resistor $R_3$ and capacitor $C_1$ are not terribly critical, they must be within those guidelines. Since all of the diodes 38, 40 and 62, 64 of the circuitry are essentially nonconducting in the receive cycle or mode, and since FET 54 possesses a very large input impedance, the only substantive contributors to the transducer load impedance are resistors $R_2$ and $R_3$, and capacitor $C_1$. Therefore, the value of 10 kilo-ohms for resistor $R_3$ has been found to be satisfactorily within acceptable range.

It is also to be understood that output 44 from FET buffer 46 can be connected to a broad band pre-amplifier, such as one made by Comlinear. However, it should also be understood that use of FET buffer 46 is optional and depends upon the circuit arrangements of the electrical components following it. In the preferred embodiment of FIG. 5, the values of the resistances used in FET buffer 46 produce an output impedance of about 120 ohms. Lower output impedances can be obtained using other values used for resistors $R_4$ and $R_5$.

FIG. 5 therefore depicts an actual embodiment of the electrical circuitry which presents a low impedance transmitter and electrical pathway to the transducer in the transmit cycle, and presents a high impedance electrical pathway to an output from the transducer in the receive cycle. It is to be understood that other embodiments are possible, but they must use the same logical structure for the transmit/receive switch, as described herein.

Experimental results of the operation of such circuitry will be described below with reference to FIGS. 6A and B through 14A and B. Unipolar pulses were generated implementing standard, commercially available piezoelectric transducers using a water immersion technique and a flat metal reflector that could be placed at prescribed distances from the transducer, all as is known in the art. After reflection from the metallic reflector, received signals were taken from the transmit-receive circuitry shown in FIG. 5, amplified in a Comlinear pre-amplifier with a 3dB bandwidth of 150 MHz, digitized in a Tektronix 7912 analog-to-digital (A/D) converter, and displayed using appropriate software in a Tektronix 4052A computer. As will be pointed out, the results were obtained both with and without FET buffer 46.

Figure 6A:
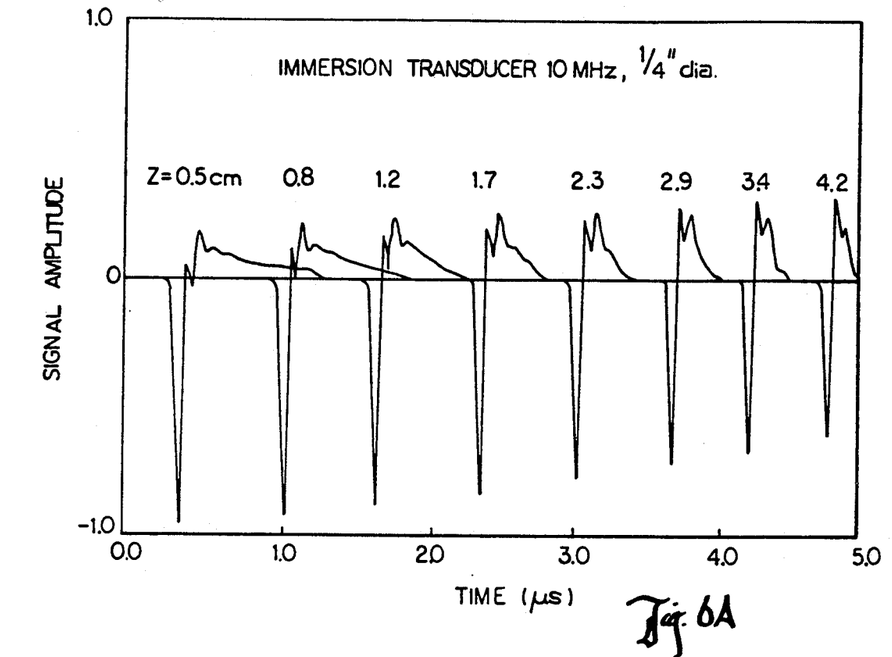
FIG. 6A is a graphic depiction of received ultrasonic pulses in the pulse-echo mode at various transduce-reflector distances using a ten Mega Hertz (MHz), ¼ inch diameter immersion transducer, with the field effect transistor (FET) of FIG. 5 by-passed.
Figure 7A:
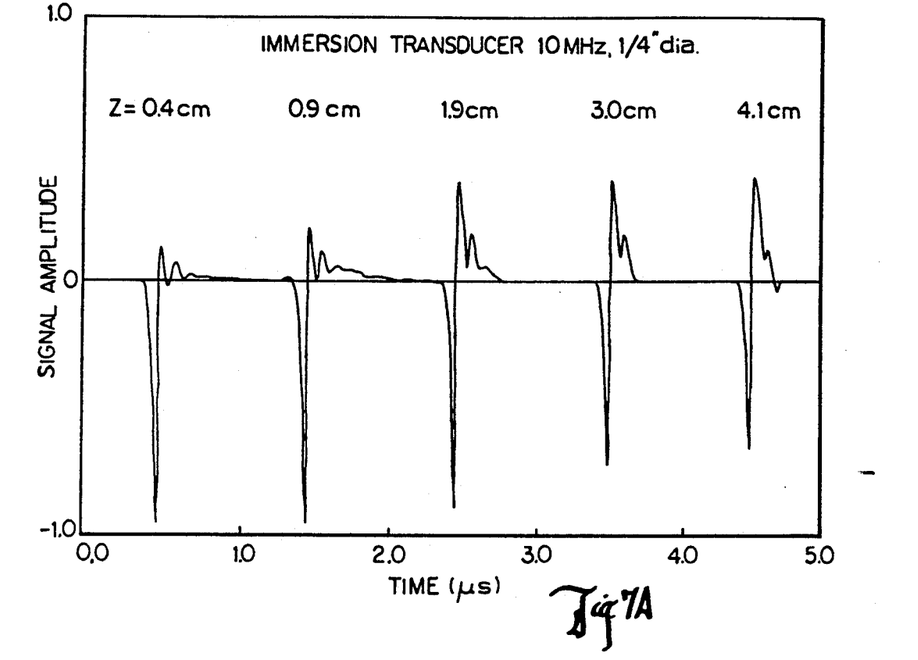

FIGS. 6A and 7A depict digitized and displayed results obtained for the 10 MHz, ¼ inch immersion transducer, showing the received time domain pulses taken at several distances between transducer face and metallic reflector. FIG. 6A shows the results in which the FET buffer is by-passed, whereas FIG. 7A shows the result with the FET buffer included.

Figure 6B:
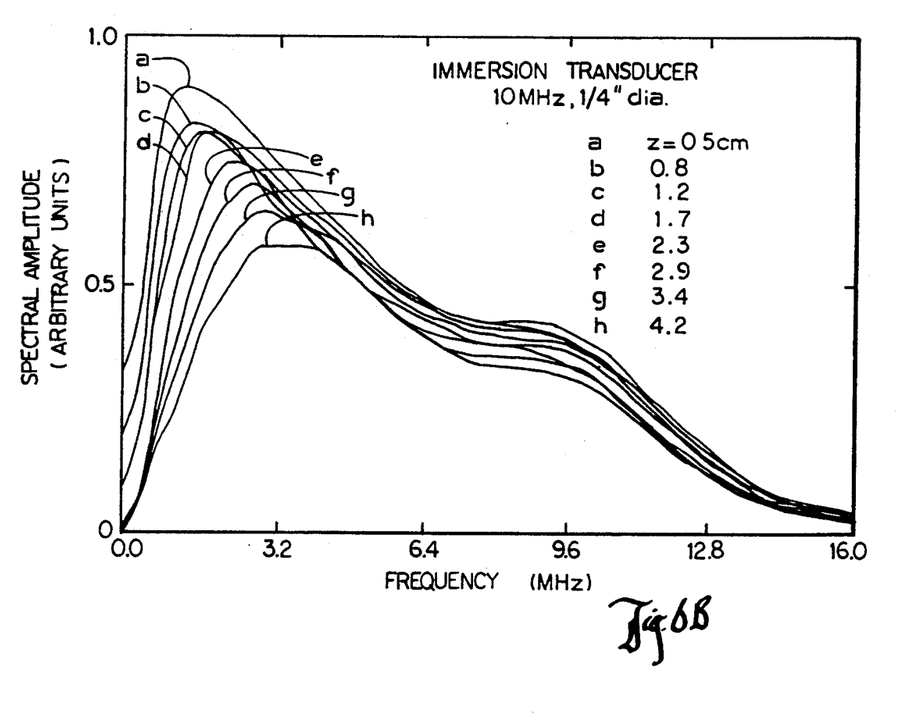
FIG. 6B are frequency spectra of the ultrasonic pulses shown in FIG. 6A.
Figure 7B:
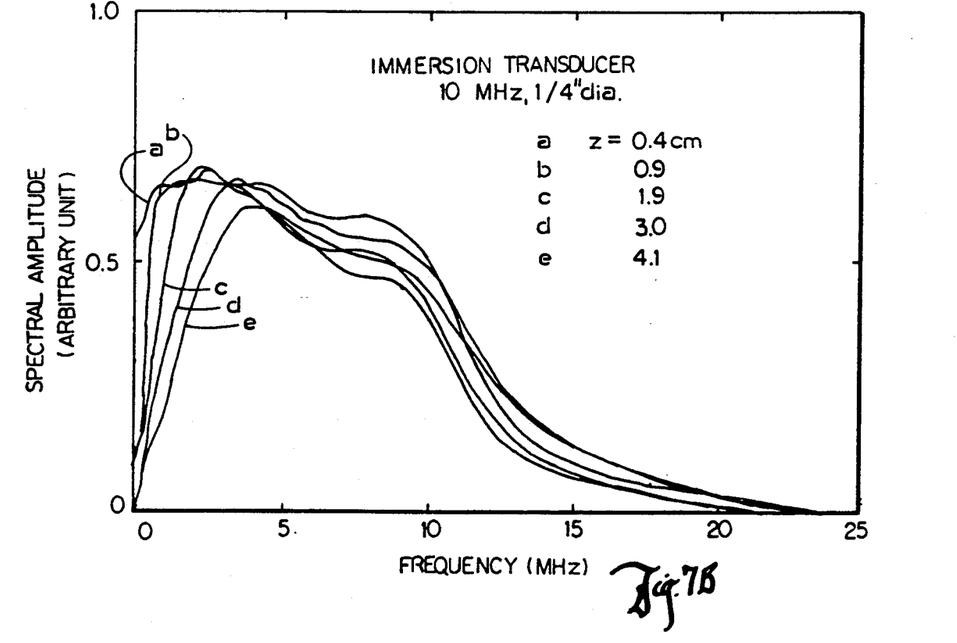
FIG. 7B are the frequency spectra of the utrasonic pulses shown in FIG. 7A.

FIGS. 6B and 7B depict a spectral analysis of the time domain pulses for the respective corresponding distances in FIGS. 6A and 7A.

It can be seen that acceptable unipolar pulses are produced at close distances in FIG. 6A, but that with increasing separation of the transducer from the reflector, the unipolar pulse degrades towards a bi-polar behavior. It would appear that this results from the loss of low frequency content because of diffraction based on the results shown in FIG. 6B. It is to be understood that the small, sharper spikes on the positive side of the negative going pulse in FIG. 6A appear to be associated with internal reverberations in the piezoelectric transducer due to imperfect backing. The results in FIG. 6B also show the signal enhancement at 10 MHz is due to the quarter wave plate which is present in the immersion transducers used.

FIG. 7A depicts the quality of the unipolar pulse produced by the present invention. It is presumed that this result is because of better matching of the transmit-receive circuitry to the cable-connected Comlinear pre-amplifier. It is pointed out that FIG. 7B shows that diffraction losses are observed in this case also, resulting in degradation in pulse shape.

Figure 8A:
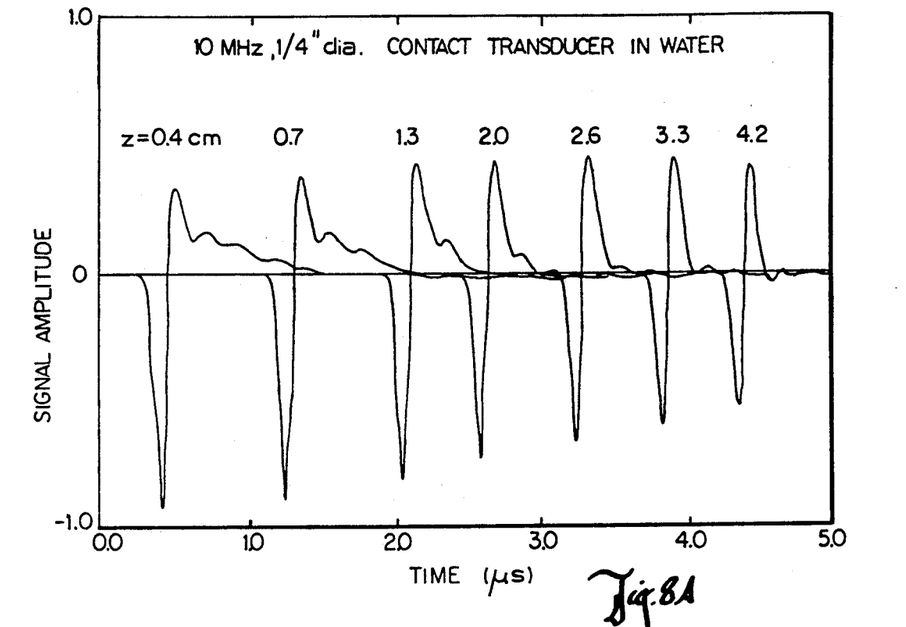
FIG. 8A is a schematic depiction similar to that of FIGS. 6A and 7A, except that a ten MHZ, ¼ inch diameter contact transducer is utilized in the immersion mode. The FET buffer of FIG. 5 is bypassed.
Figure 8B:
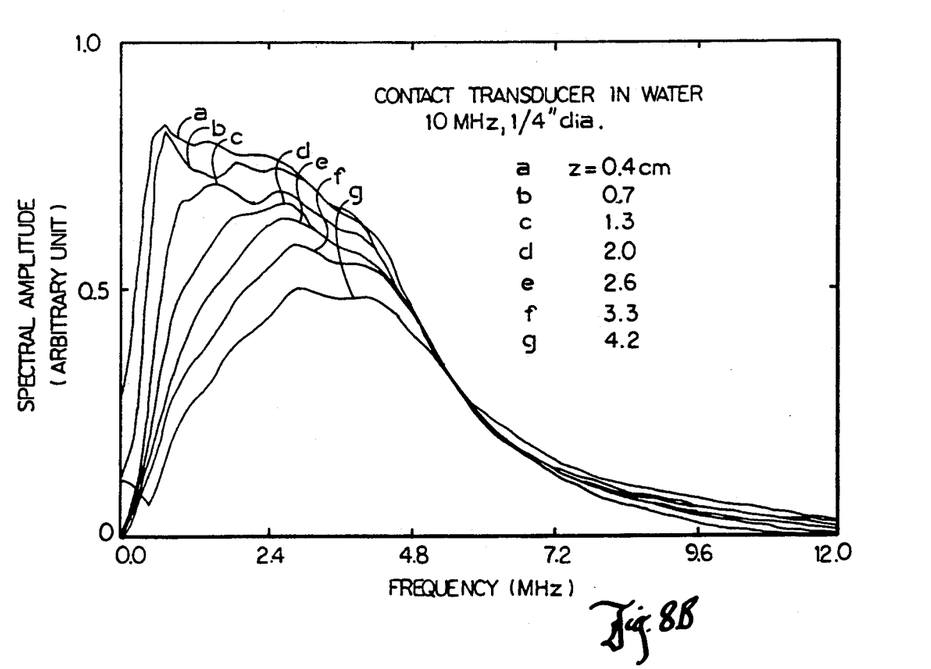
FIG. 8B depicts frequency spectra of the ultrasonic pulses shown in FIG. 8A.

By way of comparison, the same data as set forth in FIGS. 6A, 6B and 7A, 7B were obtained for a contact transducer used in an immersion mode (10 MHz, ¼ inch diameter transducer), and these results are shown at FIGS. 8A and 8B. The results were obtained with the FET buffer by-passed. It is to be understood that a contact transducer is not intended for immersion applications and does not possess a matching quarter wave plate, which is evident because of the omission of signal enhancement at 10 MHz, which can be seen by comparing the results of FIGS. 6 and 7. However, omission of this plate does not appreciably affect the generation of the unipolar pulse.

It is believed that the overshoot on the positive side of FIG. 8A is the result, in part, of by-passing the FET buffer, but also may be the result of poor matching of the backing material in that particular transducer.

It will be noted at this point that diffraction correction techniques can be used to reduce all of the spectral results to a common curve for a particular transducer. The degradation of low frequency content of the unipolar pulse signal with increasing separation between transducer and reflecting plate is an expected effect in terms of diffraction losses.

Figure 9:
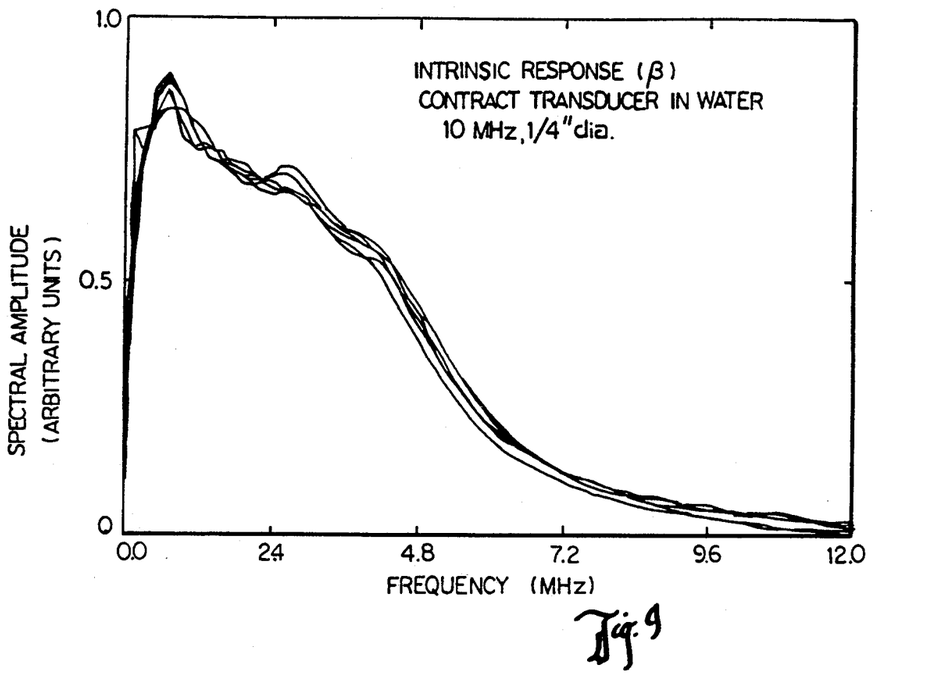
FIG. 9 is a graphic depiction of the intrinsic frequency spectrum of the unipolar ultrasonic pulse obtained by applying the diffraction corrections to the frequency spectra shown in FIG. 8B.

FIG. 9 depicts the result of diffraction correction when applied to the spectral results of FIG. 8B. This example shows that a universal curve is produced showing the true spectral response of the particular transducer for the applied voltage step function condition.

An alternative to diffraction correction is to attempt to reduce the diffraction losses. One method by which this can be accomplished is to utilize a long focal length lens attached to the transducer.

As shown in ghost lines in FIG. 1, an optional lens 66 could be utilized with a planar transducer. Lens 66, in this embodiment, was cast from epoxy to the desired radius of curvature for a 23 centimeter focal length, and then cut to an edge thickness of 0.012 inches using a diamond saw. For test purposes, lens 66 was bonded to the transducer face with glycerine.

Figure 10A:
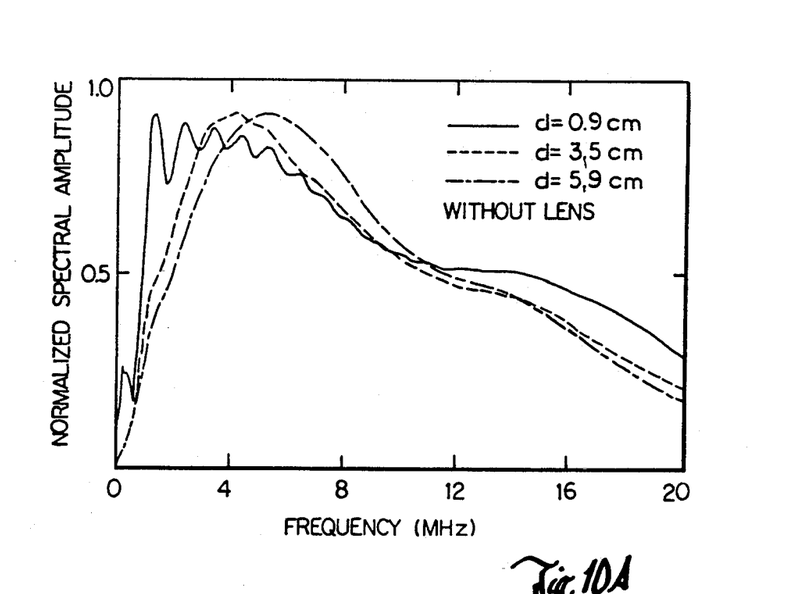
FIG. 10A is a graphic depiction of frequency spectra ultrasonic pulse-echo signals at three transducer-reflector distances without a lens. The spectra are normalized to have the same peak value. The transducer used is a 15 MHz, ¼ inch diameter immersion transducer.
Figure 10B:
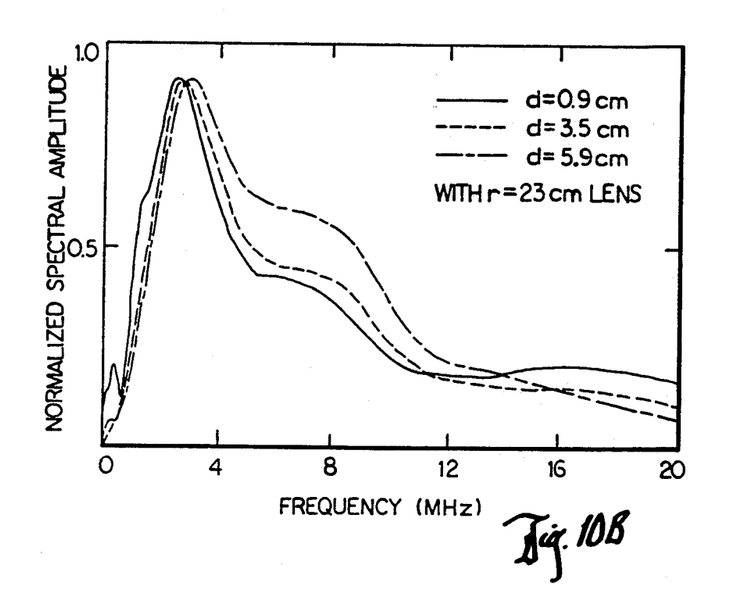
FIG. 10B is similar to FIG. 10A except the results are derived with use of a 23 centimeter focal length lens.

FIGS. 10A and 10B show the spectral results without lens 66 and with lens 66 respectively. It is obvious that the lens action helps to provide beam collimation and suppresses diffraction losses.

The alternative of reducing diffraction losses is attractive because diffractive corrections do not restore lost energy into the interrogating ultrasonic beam. This lost energy directly translates into a degraded signal-noise ratio at the lower end of the frequency spectrum. It is believed this can be remedied by use of lens such as lens 66.

It can therefore be seen that the present invention achieves its objects of providing a convenient way to obtain broadband, ultrasonic pulses usable by pulse-echo measurement techniques with a variety of standard or conventional transducers. The preferred embodiment electronic circuitry can be assembled and used separately or can easily be incorporated into existing voltage pulser units.

Two important conditions exist for satisfactory operation of the preferred embodiment of the invention. First, the transducer must not contain an inductive tuning element. Secondly, the applied voltage pulser used as a driver must be capable of providing sufficient current so that the step function pulse applied to the transducer is sharply formed.

It has been found that the top frequency limit of the transducer's band width is effectively defined by the high frequency roll-off of the piezoelectric resonance. On the other hand, the low frequency pass band limit is determined by the values of the components in the electrical circuitry utilized; here, the circuitry of FIG. 5.

Figure 11:
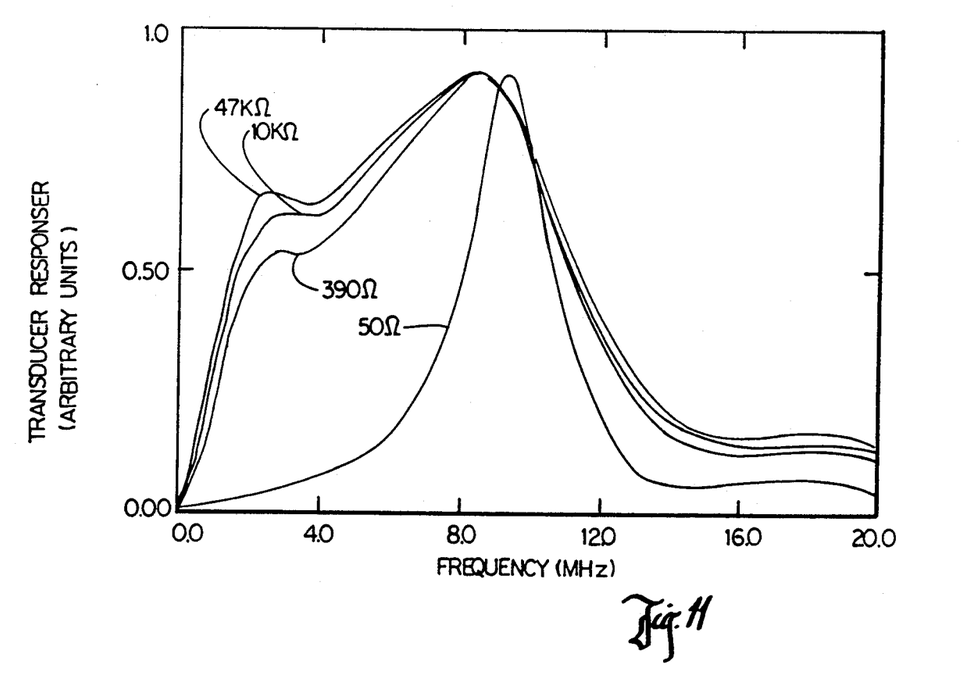
FIG. 11 is a graphic depiction of frequency spectra of a 10 MHz, ¼ inch diameter immersion transducer placed six centimeters from a flat reflector and operated in a pulse-echo mode using the transmit-receive switch of FIG. 5. The curves correspond respectively to $R_3=50$, 390, 10K and 47K $\Omega$ (ohms) as shown.

By referring to FIG. 11, the magnitude of the transducer bandwidth improvement obtained can be seen. The curves labeled 47 kilo-ohms, 10 kilo-ohms, 390 ohms, and 50 ohms, represent the pulse-echo response for a 10 MHz, ¼ inch immersion transducer with the reflector placed 6 centimeters from the transducer. The four different ohm values represent four different values for resistance $R_3$ in FIG. 5. No diffraction corrections have been applied to these results. Improvement in bandwidth is very significant across this range. It is particularly apparent that increases in $R_3$ above 10 kilo-ohms produce only small changes in the overall bandwidth, and at the expense of lengthened time constants.

The results of the present invention are also tested by comparing the measured scattering amplitude with theoretical predictions for a well-defined ultrasonic target.

Figure 12:
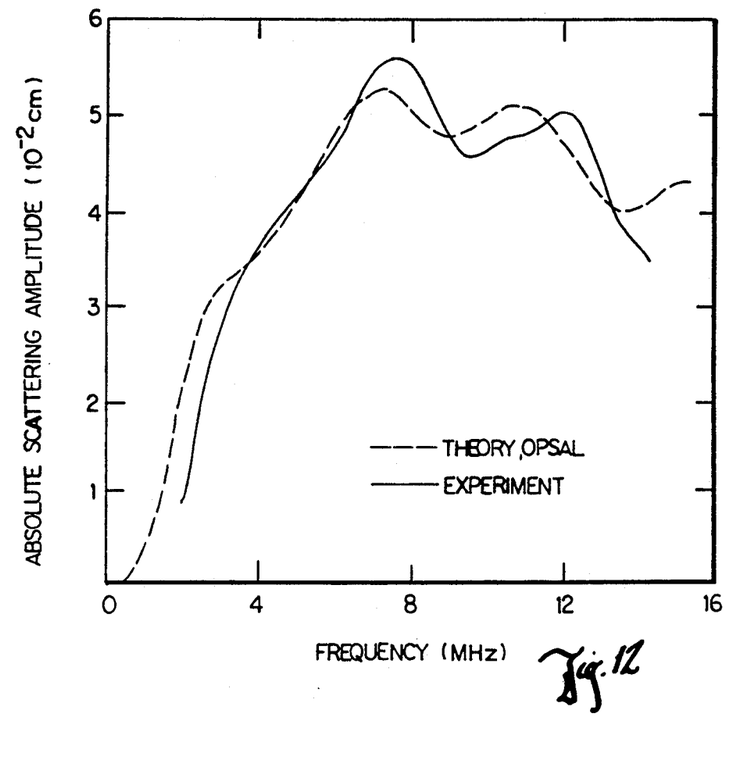
FIG. 12 is a graphic depiction of absolute scattering amplitude of an oblate spheroidal cavity in titanium with semiaxes of 400 and 200 micrometers. The dashed curve is the theoretical result and the solid curve is the experimental result obtained with the unipolar pulse in the pulse-echo mode.

As shown in FIG. 12, the solid curve shows experimental results obtained using the unipolar pulse in pulse-echo mode; whereas the broken line represents a calculated scattering amplitude in theory by Opsal, as discussed in J. L. Opsal, Journal of Applied Physics, (1985) 58: 1102. For this test, the target was a machined ellipsoidal void that was diffusion bonded in a titanium block. The ellipsoidal void was oblate in shape and the nominal values of the semi-axes were 400 microns, 400 microns and 200 microns. The curves are given in absolute units and include diffraction and attenuation corrections. The correlation of the curves is believed to be very satisfactory, and such correlation would not have been possible had the low impedance curve of FIG. 11 been used.

The included preferred embodiment is given by way of example only, and not by way of limitation to the invention, which is solely described by the claims herein. Variations obvious to one skilled in the art will be included within the invention defined by the claims.

Applications of the present invention are numerous. A first application of particular interest is ultrasonic, non-destructive evaluation of materials to investigate for internal flaws. Reference can be taken to co-owned, co-pending application Ser. No. 865,775, by inventors Thompson and Wormley, filed May 21, 1986 which discusses use of ultrasound in determining flaw size, shape and orientation, and which is hereby incorporated by reference.

Figure 13:
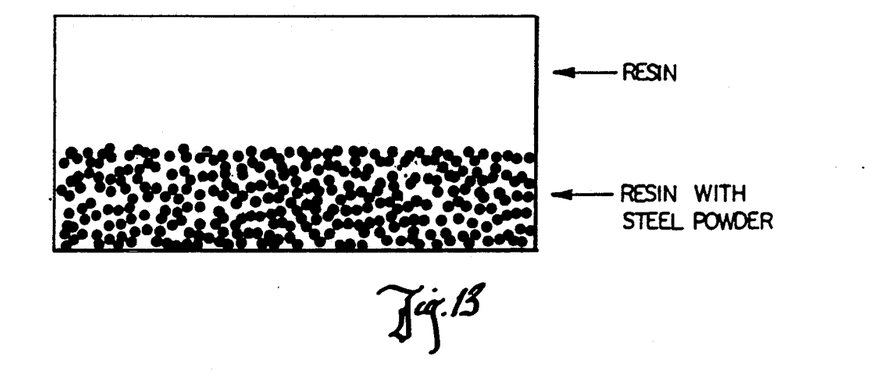
FIG. 13 depicts schematically a model specimen containing a small (6%) acoustic impedance change to simulate a "fuzzy" boundary in a material.
Figure 14A:
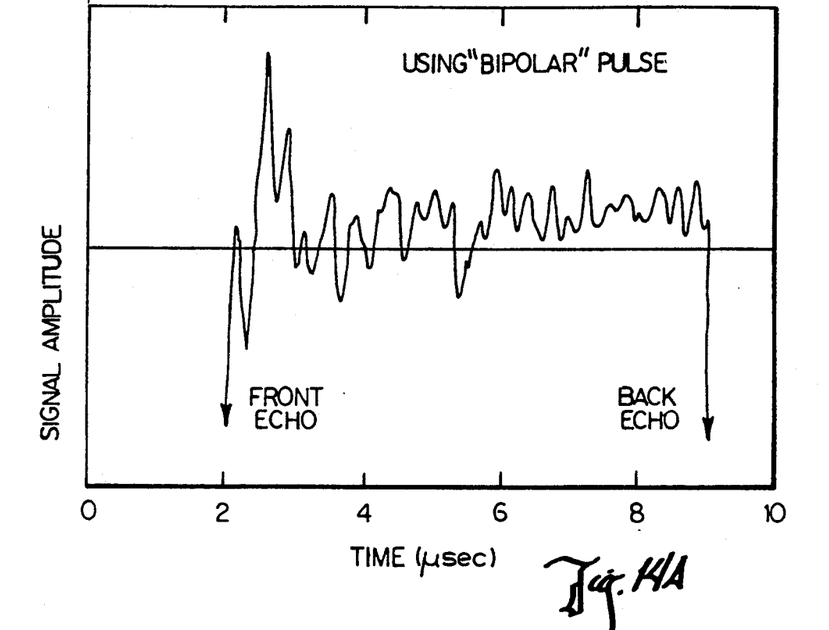
FIG. 14A is a graphic depiction of the detection of the "fuzzy" boundaries shown in FIG. 13 with a bipolar ultrasonic pulse. The signal arising from the "fuzzy" boundary is the negative-going peak approximately midway between the front surface echo and the back surface echo.
Figure 14B:
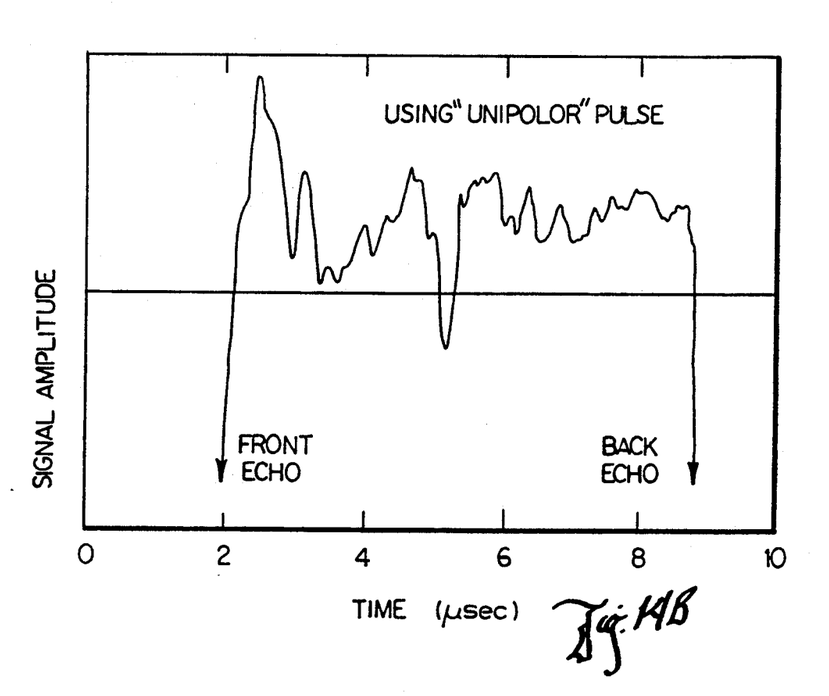
FIG. 14B is similar to FIG. 14A except it is using a unipolar ultrasonic pulse. The signal-to-noise ratio of the "fuzzy" boundary signal is clearly improved by using the unipolar pulse.

A second application is the evaluation and measurement of material properties that display a gradient in the acoustic impedance, as discussed by Yu et al., "IEEE Ultrasonic Symposium Proceedings" 1979, 284–288; and Corones, et al., Journal of Acoustic Society of America, 74(5), 1535 (1983). Such an example is schematically depicted at FIG. 13. Stainless steel beads in the 15-90 micron size range were embedded in the lower portion of an acrylic resin. This provided a "fuzzy" boundary between the clear and loaded materials with a mismatching acoustic impedance ratio of 1.06. To depict the potential benefit of the present invention, FIG. 14A shows schematically the results of ultrasonic inspection by a standard bi-polar pulse, whereas FIG. 14B shows the same inspection by a unipolar pulse. The "fuzzy" boundary echo, a negative-going peak at $t=5$ $\mu$sec or so, is clearly more pronounced with the unipolar pulse (FIG. 14B) than the bi-polar pulse (FIG. 14A).

A further example of use of the invention might be to detect boundary layer between two fluids. Many other possible uses are available.

What is claimed is:

1. A switch means for generating and detecting broadband generally unipolar ultrasonic pulses in a conventional planar transducer having a backed piezoelectric resonator with no inductive tuning, operated in a pulse-echo manner electrically connecting the transducer to a step function applied voltage pulse from a low output impedance applied voltage pulser means to generate an ultrasonic stress pulse during a transmit cycle, and electrically connecting the transducer to a high input impedance receiver means in a receive cycle, comprising:

first diode limiter means positioned between the transducer and the pulser means for maintaining a low impedance conducting pathway to the transducer during the transmit cycle, but effectively blocking the pulser means from the transducer in the receive cycle;

a combination of second diode limiter means and first resistor means positioned in parallel with the transducer for protecting the receiver means from the pulser means during the transmit cycle; and the first resistor means preventing shorting of the applied voltage of the pulser means to ground during the transmit cycle;

an RC network means positioned between the first resistor means and the receiving means for coupling received signals from the transducer to the receiving circuit during the receive cycle;

so that a generally unipolar ultrasonic pulse is maintained whether generated as an ultrasonic stress pulse or received as an ultrasonic echo by the transducer and pulses are substantially broadband in nature.

2. The switch means of claim 1, wherein the first and second diode means comprise first and second diodes connected in parallel but in opposite directions.

3. The switch means of claim 1 further comprising a third resistor means positioned between the first diode means and the pulser means for keeping circuit input at ground potential when the pulser means is switched to other circuits.

4. The switch means of claim 1 wherein the receiving means includes a field effect transistor means.

5. The switch means of claim 4 further comprising a preamplifying means connected to the field effect transistor buffer means.

6. The switch means of claim 1 wherein the value of the first resistor means is several times larger than transducer input impedance at all operating frequencies.

7. The switch means of claim 1 wherein the product of R and C of the RC network has a value which effects a low frequency pass limit.

8. The switch means of claim 1 wherein the impedance of the RC network means is selected so that total load impedance to the transducer is generally 10 to 20 times source impedance of the transducer.

9. The switch means of claim 1 wherein the input impedance of the receiving means is very large compared to the output impedance of the pulser means.

10. The switch means of claim 1 wherein the pulser means is included in a housing, and the switch means is external of the housing.

11. The switch means of claim 2 wherein the pulser means has a housing and at least a portion of the switch means is included in the housing.

12. A method of generating and receiving broadband, generally unipolar ultrasonic pulses comprising:

electrically connecting a planar ultrasonic transducer between a low output impedance applied voltage pulser means and a high input impedance receiving means;

generating by a step function an applied voltage pulse to the transducer during a transmit cycle;

during the transmit cycle;
(a) presenting a low impedance conducting path between the pulser means and the transducer so that an essentially unipolar ultrasonic stress pulse is produced by the transducer;
(b) presenting a voltage limiting means between the transducer and receiving circuit for protecting the receiving circuit from the applied voltage pulse; and
(c) presenting current resistance means between the transducer and the voltage limiting means to prevent shorting of the applied voltage pulse between the pulser means and ground; and during a receive cycle;
(a) presenting a second current limiting means between the transducer and the pulser means to block in the pulser means from the transducer; and
(b) presenting an RC network between the transducer and the receiving circuit for coupling signals from the transducer to the receiving circuit.

13. The method of claim 12 further comprising placing second resistance means between the transducer and the pulser means to keep circuit input at ground potential when the pulser means is switched to other circuits.

14. The method of claim 13 wherein the current resistance means is selected to be several times larger than input impedance of the transducer at all operating frequencies.

15. The method of claim 13 wherein the values of R and C for the RC network are selected so that the product of R and C produce a desired time constant for the RC network.

16. The method of claim 13 wherein the values of R and C for the RC network are selected so that the product of R and C present a desired low frequency path limit for the RC network.

17. The method of claim 13 wherein the impedance of the RC network is selected so that total load impedance to the transducer is generally 10 to 20 times source impedance of the transducer means.

18. The method of claim 13 wherein the input impedance of the receiving circuit is selected to be very large compared to the impedance of the pulser means.

19. The method of claim 13 wherein the low impedance applied voltage pulser means and high input impedance receiving means are substantially incorporated into a unitary housing.

20. The method of claim 13 wherein the current limiting means, current resistance means, and second current limiting means, and RC network are independent of any housing for the low impedance applied voltage pulser means.

* * * * *